United States Patent [19]
Jenkins

[11] Patent Number: 6,010,401
[45] Date of Patent: Jan. 4, 2000

[54] GERM REMOVING DEVICE FOR AIR SUPPLY SYSTEMS

[76] Inventor: James H. Jenkins, 6010 N. 26th St., Arlington, Va. 22207

[21] Appl. No.: 09/065,435

[22] Filed: Apr. 24, 1998

[51] Int. Cl.[7] ................................................... F24F 13/28
[52] U.S. Cl. ....................... 454/284; 55/524; 55/DIG. 24
[58] Field of Search ..................... 55/477, 524, DIG. 24, 55/DIG. 35; 454/284, 289, 290, 291, 309, 322, 328

[56] References Cited

U.S. PATENT DOCUMENTS

| | | |
|---|---|---|
| 2,027,906 | 1/1936 | Hand . |
| 2,770,316 | 11/1956 | Wilson et al. . |
| 2,978,068 | 4/1961 | Pierfederici . |
| 3,290,868 | 12/1966 | Upor . |
| 3,768,235 | 10/1973 | Meyer et al. . |

*Primary Examiner*—Harold Joyce

[57] ABSTRACT

A device for catching and removing germs, viruses and the like from air flowing in an air path of an air supply system. The device includes a cylindrical member or members mounted in the air flow path so that air passing along the air flow path impinges on the periphery of the germ and virus catching and removing member or members to reduce the presence of germs, viruses, contaminants and the like from the air.

7 Claims, 3 Drawing Sheets

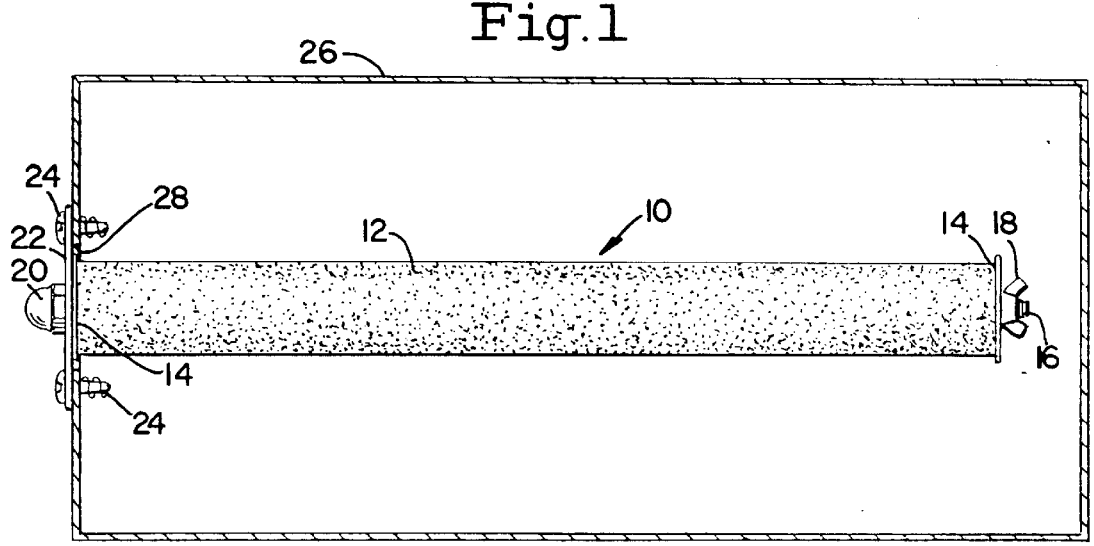
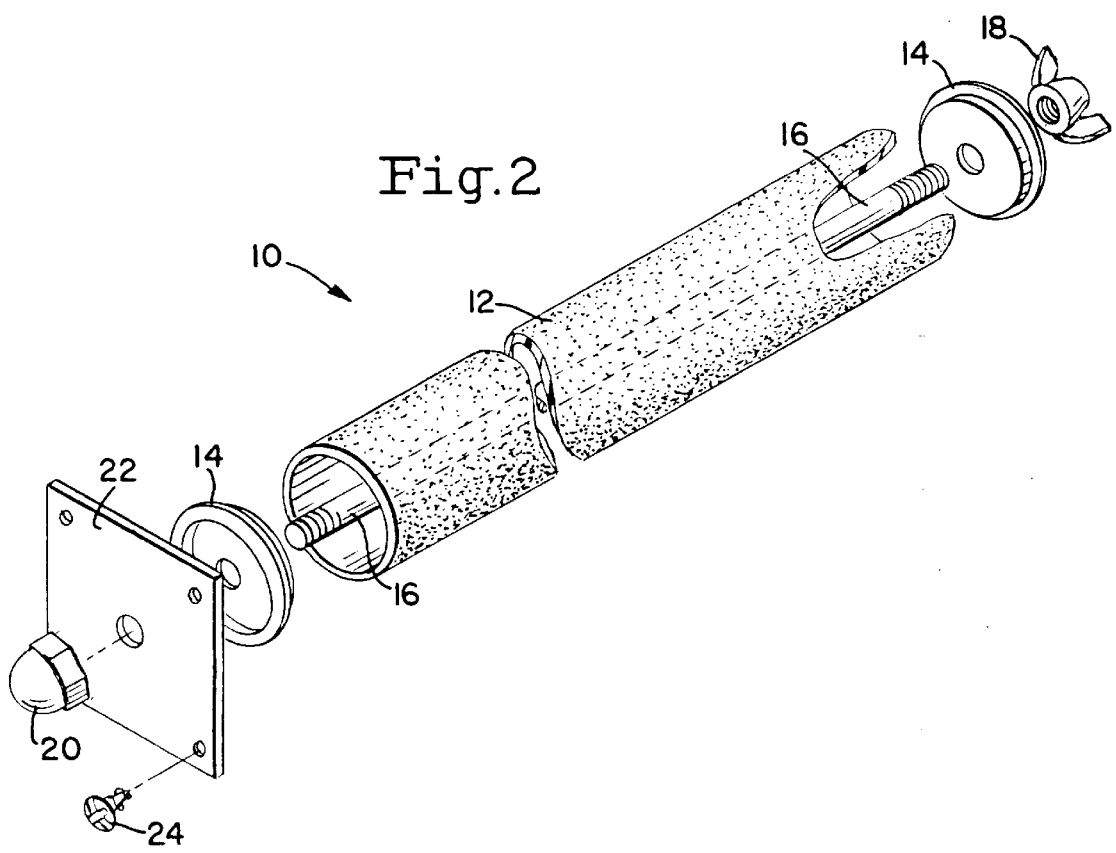

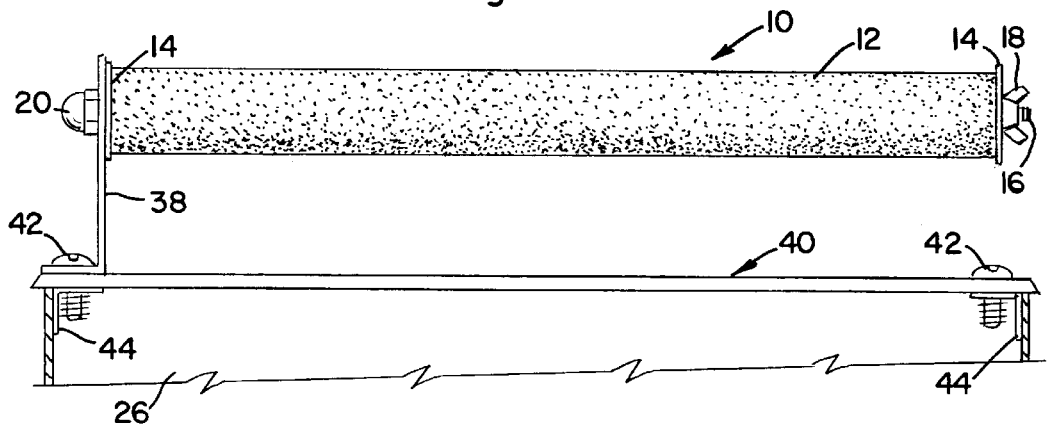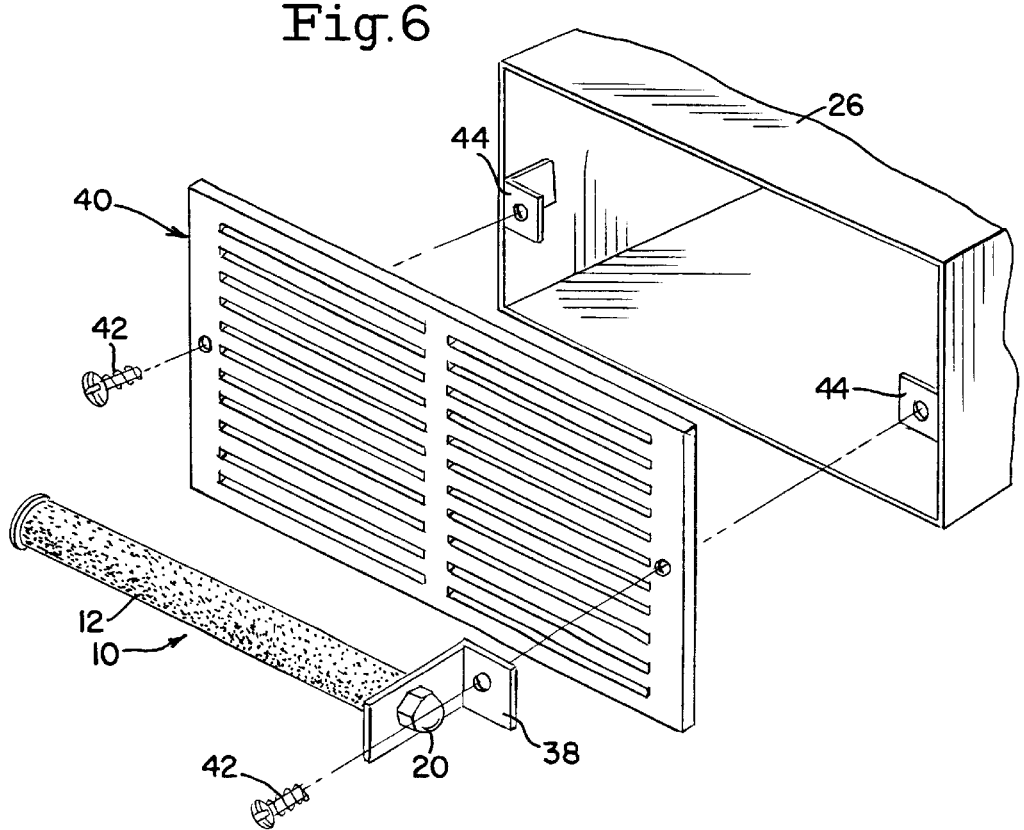

GERM REMOVING DEVICE FOR AIR SUPPLY SYSTEMS

BACKGROUND OF THE INVENTION

1. Field of the Invention

The present invention relates to a device for catching and removing germs, viruses and the like from air flowing through an air duct or discharged from an air duct. The device includes a cylindrical member or members mounted in the air flow path so that air passing along the air flow path impinges against the surface of the germ and virus catching and removing member or members.

2. Description of the Prior Art

Air ducts and air supply systems are provided with various types of filters for removing particulate material and the like and also are provided with humidifiers or dehumidifiers for supplying moisture or removing moisture from the air in the air supply system. However, the mounting of a device for catching and removing germs, viruses and the like within the air duct, on the exterior of the discharge register, on the exterior of an intake register or on the interior of a duct register is unique and not known in the prior art.

SUMMARY OF THE INVENTION

The invention includes the mounting of a cylindrical member or plurality of cylindrical members in the air path in an air supply system or associated with the register that discharges air or intakes air into the air supply system. The basic embodiment of the invention includes a single cylindrical member mounted on a plate removably mounted over a hole in a portion of the peripheral wall of an air duct with the plate being removable along with the cylindrical member to enable replacement thereof. The cylindrical member is mounted on a central rod with fasteners at each end thereof for enabling the cylindrical member to be replaced. The exterior of the cylindrical member is provided with an adhesive material and may include bactericides, fungicides, and the like to collect and remove bacteria, germs, viruses as well as particulate contaminants thereby cleaning the air and removing germs and viruses from the air flowing through the air supply system. The invention also includes the use of multiple cylindrical members oriented in a manner that substantially all of the air flowing through the air supply system will impinge on the cylindrical members.

Accordingly, an object of the present invention is to provide a device for removing germs and viruses from the air flowing through an air supply system which includes a removable and replaceable cylindrical member or members oriented in an air duct in the flow path of air passing therethrough or mounted on a register connected to the air duct.

Another object of the invention is to provide a device in accordance with the preceding object in which each member is in the form of a cylindrical removable member provided with characteristics for collecting germs, viruses and capable of being easily and inexpensively replaced.

A further object of the invention is to provide a device in accordance with the preceding objects in which the member or members are mounted on a plate available from the exterior of the air supply system or by brackets mounted exteriorly of a register to removably support the cylindrical members in position that air impinges upon the member or members as the air flows through the air supply system.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a transverse, sectional view of a typical air duct illustrating the virus and germ removing device of the present invention.

FIG. 2 is an exploded group perspective view, with portions broken away, illustrating the structural components of the device.

FIG. 5 is a top plan view of a virus and germ removing device mounted exteriorly of an air register at the terminal end of a duct.

FIG. 6 is an exploded group perspective view of the device illustrated in FIG. 5.

DESCRIPTION OF THE PREFERRED EMBODIMENT

Figure 3:
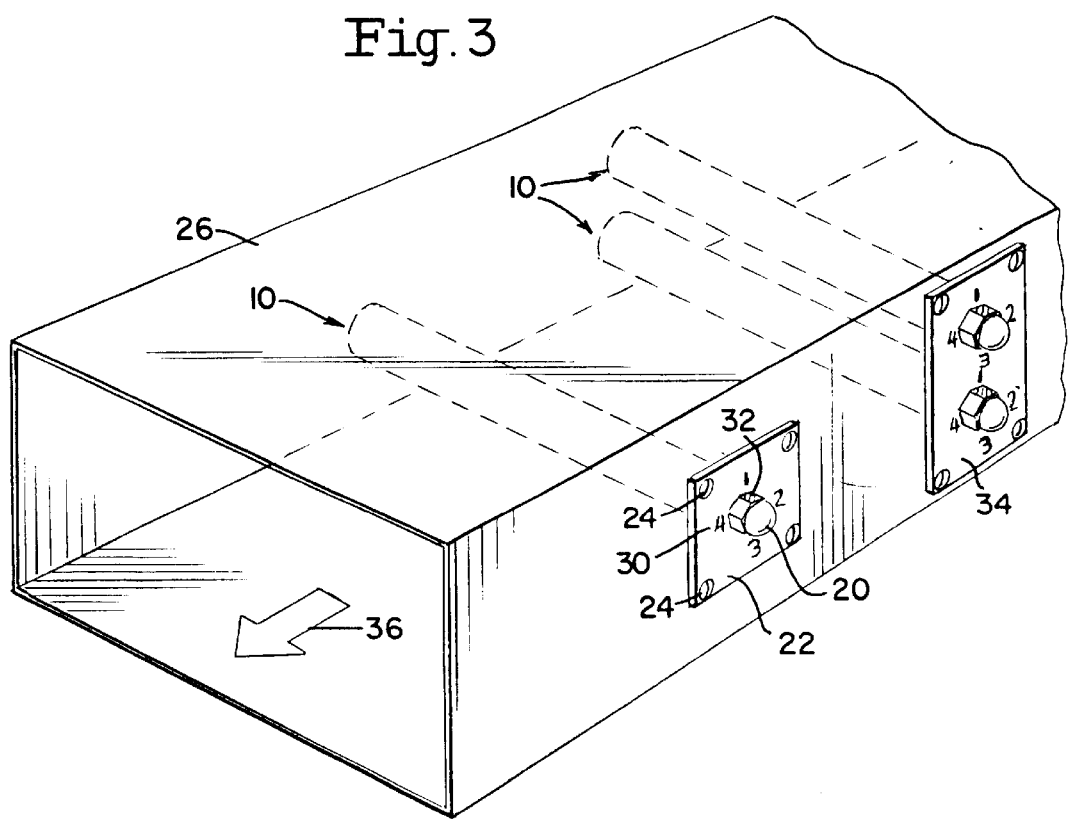
FIG. 3 is a perspective view of an air duct illustrating a second embodiment of the invention in which multiple devices are installed in an air duct.

Although only one preferred embodiment of the invention is explained in detail, it is to be understood that the invention is not limited in its scope to the details of construction and arrangement of components set forth in the following description or illustrated in the drawings. The invention is capable of other embodiments and of being practiced or carried out in various ways. Also, in describing the preferred embodiment, specific terminology will be resorted to for the sake of clarity. It is to be understood that each specific term includes all technical equivalents which operate in a similar manner to accomplish a similar purpose.

Referring now specifically to the drawings, the virus and germ catching and removing device of the present invention is generally designated by reference numeral 10 and includes a cylindrical member 12 having an adhesive coating on the external surface thereof. The tubular or cylindrical member 12 may be of plastic, metal, cardboard or the like and the coating may be adhesive and may be impregnated with various agents to kill germs, virus and the like. The cylindrical member 12 includes end caps 14 and a centrally disposed support rod 16 which is threaded on each end with a wing nut 18 threaded onto one end of the rod 16 and a cap nut 20 threaded onto the other end thereof. The end of the rod 16 having the cap nut 20 thereon extends through a central aperture in a mounting plate 22 which is secured to the side wall of the air duct 26 as illustrated in FIG. 1 by fasteners 24 such as sheet metal screws or the like. The mounting plate 22 is provided with a central opening and the wall of the air duct 26 is provided with an opening 28 which is sufficiently large to enable the assembled germ and virus removing device 10 to be inserted into and removed from the air duct 26. This enables the virus and germ removing device to be inserted into the air duct 26 and easily mounted therein and also easily removed for replacement of the cylindrical member 12. The exterior of the mounting plate 22 is provided with numerical indicia 30 around the periphery of the cap nut 20 and the cap nut 20 is provided with a color indicator 32 on one flat surface thereon for alignment with the indicia 30. The indicia 30 includes numerals 1, 2, 3 and 4 which together with the color indicator 32 enables the cylindrical member 12 to be rotated to indicate the portion of the periphery of the cylindrical member 12 facing the direction of air flow in the air duct 26. The air flow direction is designated by reference numeral 36 in FIGS. 3 and 4.

Figure 4:
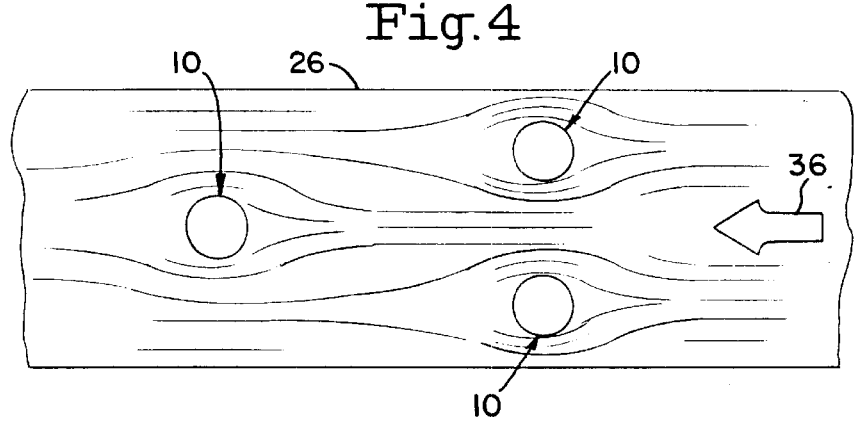
FIG. 4 is a schematic elevational view illustrating the positioning of the virus and germ removing devices in relation to the air flow past the devices.

FIGS. 3 and 4 also indicate a form of the invention in which multiple virus and germ removing devices 10 are installed in the air duct 26 with the position of installation being illustrated schematically in FIG. 4. The same reference numerals are utilized for each of the germ and virus removing devices 10. The three germ removing devices 10 are oriented with two of the devices upstream and one of the devices down stream with the upstream devices being closer to the top and bottom walls of the air duct 26 and the down stream device 10 being centrally located between the top and bottom walls so that air flow in the direction of arrow 36 will pass around the upstream removing devices 10 and around the down stream removing device 10 in the manner schematically illustrated in FIG. 4.

FIGS. 5 and 6 illustrate an embodiment of the virus and germ removing device 10 mounted by a supporting bracket 38 externally of a register or vent at the terminal end of an air duct 26. The mounting bracket 38 is generally of L-shaped configuration and has an aperture in alignment with the normally provided apertures in the air register or vent 40 for receiving mounting screws 42 which extend into and are secured to mounting brackets 44 in the air duct which are normally provided for mounting the air register or vent 40 to the end of the air duct 26. In this construction, the bracket 38 supports one end of the virus and germ removing device 10 with the cylindrical member being generally parallel to the surface of the air register or vent 40 generally at the center between the upper and lower edges. In this embodiment of the device, multiple virus and germ removing devices 10 may be supported externally of the air register or vent or may be mounted internally thereof by appropriate bracket structure attached to the interior of the vent or register 40.

The cylindrical member 12 and its related supporting structure is constructed somewhat in the manner of a paint roller but the smooth exterior surface of the cylindrical member 12 is provided with an adhesive coating which will retain and remove viruses, germs and the like from the air flowing through the air duct, or from air being discharged from the register or vent or air entering the air duct through the register or vent. The material on the exterior of the cylindrical member may be impregnated with bactericide, fungicide or similar materials for removing and rendering harmless various germs, bacteria, viruses and the like thereby enabling areas being supplied air by the air supply system to be provided with a germ free and virus free ambient air.

The foregoing is considered as illustrative only of the principles of the invention. Further, since numerous modifications and changes will readily occur to those skilled in the art, it is not desired to limit the invention to the exact construction and operation shown and described, and, accordingly, all suitable modifications and equivalents may be resorted to, falling within the scope of the invention.

What is claimed as new is as follows:

1. A virus and germ catching, collecting and removing device for an air supply system in the form of an air duct, said device comprising a cylindrical member extending into the interior of an air duct, said cylindrical member having an adhesive exterior coating, a mounting plate for said cylindrical member mounted exteriorly of the air duct, said air duct including an opening to enable insertion and removal of the cylindrical member for replacement thereof.

2. The device as defined in claim 1 wherein said mounting plate is removably supported on the exterior of an air duct.

3. The device as defined in claim 2 wherein said cylindrical member includes a central support rod, said support rod including a pair of end caps supporting the cylindrical member on the support rod in concentric relation to the support rod, fastening devices on the support rod securing the end caps in place.

4. The device as defined in claim 3 wherein said support rod includes a threaded end extending through the mounting plate, a cap nut securing the support rod on the mounting plate, indicating structure on the cap nut and mounting plate to indicate the portion of the cylindrical member facing the path of air flowing through the air duct.

5. A virus and germ catching, collecting and removing device for an air supply system in the form of an air duct, said air duct including an air register incorporated therein, a cylindrical member mounted on said air register in the air flow path through the air duct, said cylindrical member having an adhesive exterior coating.

6. The device as defined in claim 5 wherein said cylindrical member is mounted externally of the register, a mounting bracket securing the cylindrical member to the air register in spaced parallel relation to a central portion thereof.

7. A virus and germ removing device for an air supply system comprising a plurality of cylindrical members mounted in the interior of an air duct in the air flow path, said cylindrical members being spaced vertically in relation to each other to form a pair of cylindrical members and a third cylindrical member spaced laterally from the pair of vertically spaced cylindrical members and oriented in alignment with the space between the pair of vertically spaced members whereby air flow is engaged with surfaces of the cylindrical members substantially throughout the vertical and horizontal extent of the transverse configuration of the air duct, each of said cylindrical member having an adhesive exterior coating and being supported by externally mounted brackets detachably connected to the exterior of the air duct to enable removal and replacement of the cylindrical members.

* * * * *